(12) United States Patent  
Colome et al.

(10) Patent No.: US 9,476,022 B1
(45) Date of Patent: Oct. 25, 2016

(54) INSTRUMENTED AND CONTROLLED FERMENTATION SYSTEM AND PROCESS WITH VOC RECOVERY

(71) Applicant: EcoPAS LLC, Irvine, CA (US)

(72) Inventors: Steven G. Colome, Ojai, CA (US); Marci Norkin, Templeton, CA (US); Leonard Mark Ramsaier, Newport Beach, CA (US)

(73) Assignee: EcoPAS LLC, Irvine, CA (US)

( * ) Notice: Subject to any disclaimer, the term of this patent is extended or adjusted under 35 U.S.C. 154(b) by 228 days.

(21) Appl. No.: 14/451,353

(22) Filed: Aug. 4, 2014

Related U.S. Application Data (63) Continuation-in-part of application No. 13/358,499, filed on Jan. 25, 2012, now Pat. No. 8,794,049.

(51) Int. Cl.
*C12M 1/00* (2006.01)
*G01L 19/08* (2006.01)
*C12M 1/34* (2006.01)

(52) U.S. Cl.
CPC ............ *C12M 29/20* (2013.01); *C12M 41/40* (2013.01); *G01L 19/083* (2013.01)

(58) Field of Classification Search
CPC ....... C12G 1/02; C12M 21/12; C12M 29/20; C12M 43/02; C12P 7/06
See application file for complete search history.

(56) References Cited

U.S. PATENT DOCUMENTS

| 4,359,533 A | 11/1982 | Wilke et al. |
| 4,856,421 A | 8/1989 | Whitford |
| 4,883,759 A | 11/1989 | Hopkins |
| 4,959,228 A | 9/1990 | Skrgatic et al. |
| 5,245,405 A | 9/1993 | Mitchell et al. |
| 5,470,746 A | 11/1995 | Kim |
| 6,010,909 A | 1/2000 | Lapidus |
| 6,354,310 B1 * | 3/2002 | Farr ................. B08B 7/0021 134/105 |
| 7,004,625 B2 | 2/2006 | Egidio |
| 7,510,864 B2 | 3/2009 | Krichevsky et al. |
| 7,597,784 B2 * | 10/2009 | Bednarek ............ B01D 1/221 159/24.1 |
| 7,972,825 B2 | 7/2011 | Sovereign et al. |
| 2003/0097937 A1 | 5/2003 | Francia |
| 2004/0004717 A1 | 1/2004 | Reed |
| 2004/0039514 A1 | 2/2004 | Steichen et al. |
| 2004/0076712 A1 | 4/2004 | Rodgers et al. |
| 2004/0173449 A1 * | 9/2004 | Nadeau ................ B01D 1/305 203/2 |
| 2007/0238169 A1 | 10/2007 | Abilez et al. |
| 2007/0266632 A1 | 11/2007 | Tsangaris et al. |
| 2008/0193207 A1 | 8/2008 | Kruse et al. |
| 2008/0213874 A1 | 9/2008 | Mitchell et al. |
| 2009/0223612 A1 | 9/2009 | McKnight et al. |
| 2012/0301937 A1 * | 11/2012 | Nilsson ................ C12M 21/12 435/161 |
| 2013/0140231 A1 | 6/2013 | Novak et al. |
| 2014/0127768 A1 * | 5/2014 | Nilsson ................ C12M 21/12 435/158 |
| 2014/0251835 A1 | 9/2014 | Mitchell et al. |

FOREIGN PATENT DOCUMENTS

WO    2012/005667 A1    1/2012

* cited by examiner

*Primary Examiner* — Hezron E Williams
*Assistant Examiner* — David Z Huang
(74) *Attorney, Agent, or Firm* — Fish & Tsang LLP (57) ABSTRACT

A fermentation system include a volatile organic compound (VOC) recovery sub-system and an instrumented control devise for detecting anomalous condition with a fermentor vessel and providing alarms or alerts and controlled responses to overcome the cause of the detected anomaly.

12 Claims, 7 Drawing Sheets

INSTRUMENTED AND CONTROLLED FERMENTATION SYSTEM AND PROCESS WITH VOC RECOVERY

CROSS-REFERENCE TO RELATED APPLICATION

This application is a continuation-in-part of U.S. patent application Ser. No. 13/358,499 filed Jan. 25, 2012 which claims the benefit of U.S. provisional patent application 61/436,230 filed Jan. 26, 2011.

This application incorporates by reference the disclosure of pending U.S. patent application Ser. No. 12/476,231 filed Jun. 1, 2009 and entitled "Volatile Organic Compound Recovery System and Method."

The present invention relates to the instrumented monitoring and control of the successive states or stages of the fermentation and, more particularly, to fermentation monitoring during active yeast-based fermentation in the production of alcohol-containing beverages and other fermented subject matter, including pharmaceuticals, and, still more particularly, to monitoring of closed fermentation vessels in which carbon dioxide is released though a port or release valve as sugar is consumed and ethanol produced.

During the production of fermented alcoholic beverages, such as wine, a mixture of crushed grapes, juice, and yeast is placed in a fermentation vessel; the yeast metabolizes sugars in the grape juice (known as "must") over a period of several days to one or two weeks at a process temperature of about 60-90° F. During this fermentation period in which the liquid component of the must evolves into the new wine, both EtOH and $CO_2$ evolve in equal molar amounts as a consequence of yeast metabolism. Governed by the chemical properties of solubility, vapor pressures in the headspace, and other chemical and physical properties, the ethanol and the carbon dioxide enter the headspace within the fermentation vessel above the surface of the must.

$CO_2$ and EtOH co-evolve during the fermentation process with the volume thereof varying with time; thus, the fermentation process can be described as having many successive "states" or "stages". During the very beginning of the fermentation process after initial yeast-innoculation, the generation of $CO_2$ and EtOH is low with the volumes thereof increasing to some maximum as the process temperature rises and the sugars are consumed at some time-varying rate with the volume of $CO_2$ and EtOH thereafter diminishing as the fermentation process is completed. Historically, fermentation activity at any stage in the process has been measured by assaying samples for Brix reduction and/or by measuring temperature as a function of time. Neither Brix assaying or temperature measurement can be viewed as "real time" since the Brix assay is a chemical analysis process that is typically completed sometime after the sample is taken and the substantial heat capacity of the liquid components introduces a "thermal hysteresis" variable into the process. Additionally, Brix assaying and/or temperature measurements suffer from inhomogeneity within the fermentation tank and are subject to sampling error. Thus, Brix assaying and/or temperature measurement are sub-optimal metrics for identifying a particular state or stage of the fermentation process. In general, Brix assaying and/or temperature measurements cannot accurately identify sluggish fermentations, over-active fermentations, or sub-optimal equipment functionality (or equipment failures) quickly enough to allow for effective corrective action(s) by the wine maker to save or preserve the quality of the new wine.

The issue of instrumented monitoring and control of the fermentation process is important where pollution control equipment, such as systems for the recovery of volatile organic compounds (principally EtOH), is integrated into the fermentation process; it is important that any such recovery system do not perturb the conditions in the headspace of the fermenter, since such perturbations could be mis-interpreted as undesired anomalies by any instrumentation and control system.

SUMMARY

An instrument monitored and controlled system for passive VOC recovery in the fermentation process that does not adversely affect the conditions within the fermenter vessel and does not affect or minimally affects the conditions within the headspace of the fermenter vessel uses the production of $CO_2$ during the fermenting process as the driving energy source to move a portion of the gaseous/vaporous material in the headspace of the fermenter through an appropriately sized conduit to a chilled condensing device to condense the VOCs (principally ethanol) for recovery as a liquid and to exhaust the $CO_2$ to the atmosphere or to recover the $CO_2$ for other uses. The conduit from the headspace of the fermenter to the chilled condensing device is sized to provide a flow restriction in a selected range such that the headspace equilibria is not affected while directing the gaseous/vaporous material in the headspace to move through the conduit in response to the generation of the $CO_2$ during the fermentation process. Condensation capacity is increased or decreased as appropriate during the fermentation cycle to recover the EtOH from the headspace.

The instrumented monitoring and control arrangement obtains successive pressure measurements in the fermenter headspace from the start of the fermentation process for processing by a stored-program controlled processor with the successive data points compared to reference data point set or to known good data points with the variance indicative of a normal fermentation process, a slow or sluggish fermentation process, or an over-active fermentation process. In those instances in which a non-normal fermentation is identified, corrective action can be initiated to correct the non-normal condition. In those cases, where successive pressure measurements multiple concurrent processes, comparison of data points between the different concurrent processes can identify an anomalous process and provide an alert signal or a corrective control signal for that anomalous process.

Because a passive VOC recovery system is used (i.e., utilizing the $CO_2$ gaseous by-product of the fermentation process as the driving force to propel the EtOH vapor for its subsequent collection through variable capacity condensation) the probability of the VOC process adversely perturbing the headspace conditions in the fermenter minimizes any chance the adversely perturbed headspace conditions will cause spurious pressure readings to be obtained that could drive unnecessary corrective actions.

The benefit of successive pressure readings is that carbon dioxide is released immediately after it is produced during the sugar metabolism process and the flow thereof through the exhaust port or release valve of a closed fermentation vessel effectively integrates fermentation activity throughout the must volume.

DESCRIPTION

Figure 1:
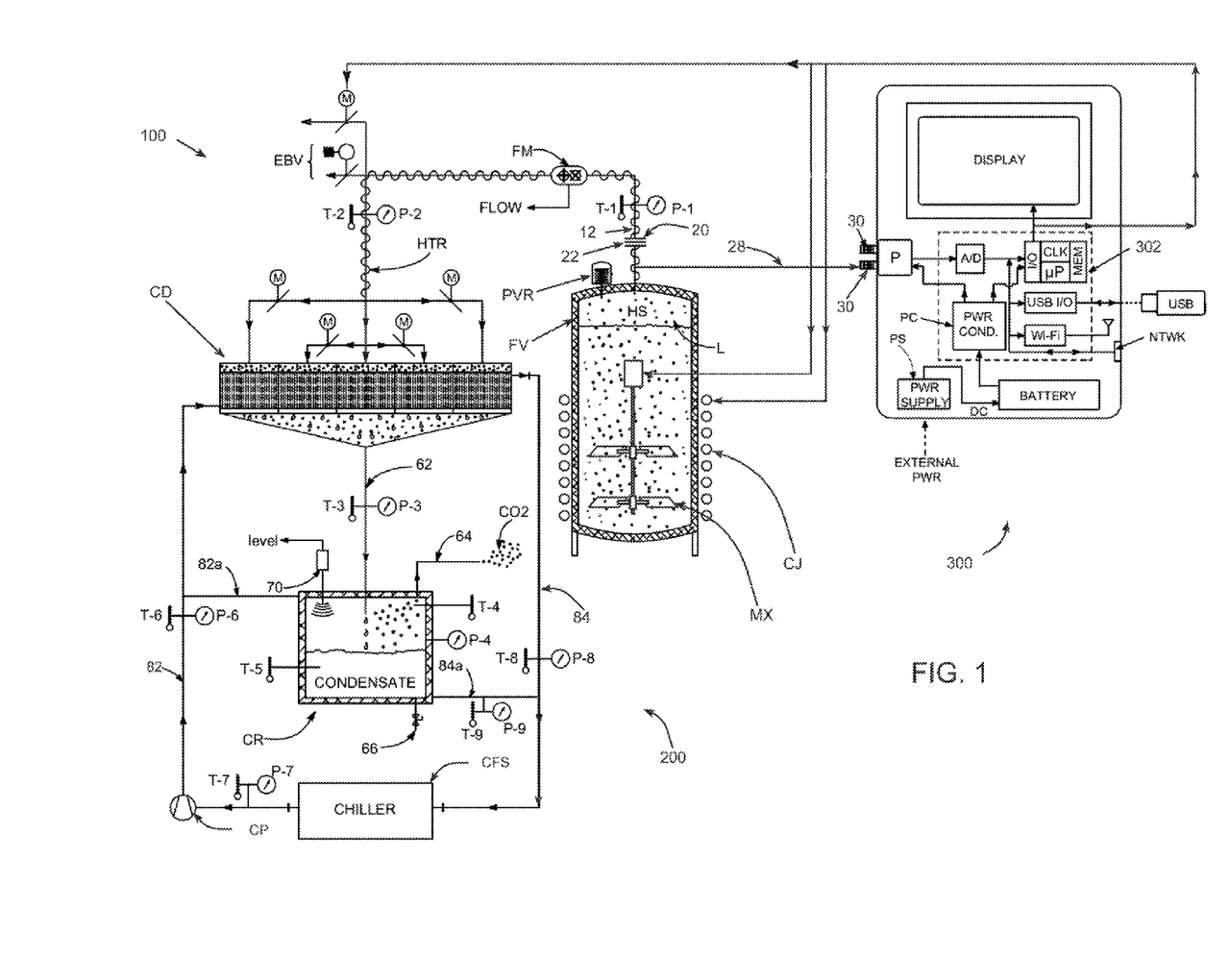
FIG. 1 is an overall system schematic including a fermentation vessel, passive VOC recovery system, and a pressure sensing and process control instrument.

FIG. 1 illustrates an exemplary system and is designated generally therein by the reference character 100 and includes a fermentation vessel FV, a VOC recovery system 200, and a instrumentation and control system. The fermentation vessel FV includes various viewing/inspection ports, hatches, and closable openings (not shown) and is typically fabricated from stainless steel, copper, or other suitable materials with a working volume or capacity of up to 600,000 gallons or more. In practice, the lower portion of the interior volume of the fermentation vessel FV is filled to some level L with liquid grape or other fruit extracts, hops, grains, and/or other fermentable feedstocks along with any other materials/additives typically used in the process. A headspace HS is left above the surface of the liquid into which water vapor, ethanol, $CO_2$, and other gases or vapors associated with the fermentation process accumulate as they are evolved during the fermentation process; in general, an equilibria is established between the liquid component and the gaseous/vaporous components in the headspace HS. In the fermentation process for wine, the yeast component metabolizes sugars in the starting material with the process proceeding on a day-by-day basis until completion. The fermentation process generates $CO_2$ and EtOH in direct molar proportion to one another in the liquid must with the gases/vapors in the headspace at a temperature of 60-90° F. or so during the process.

As shown in FIG. 1, a bleed-off conduit 12 is connected to the top of the fermentation vessel FV and is in fluid communication with the headspace HS within the fermentation vessel FV so that the pressure of the gases/vapors in the headspace HS can be measured as described below. The bleed-off conduit 12 includes a first connection interface (typically mating flanges that are connected together by sanitary fittings, (known in the industry as "triclamp" fittings), or alternatively threaded fasteners . . . ) that connects to a pressure-vacuum relief valve PVR that functions as a primary safety device for the fermentation vessel FV. A connection interface 20 that includes a orifice plate 22 positioned between the flanges thereof is positioned in the bleed-off conduit 12. Gases/vapors in the headspace HS that pass through the orifice plate 22 flow therethrough at an orifice-constrained flow rate. In addition, a pressure sense line 28 provides fluid communication with a input port 30 of a pressure sensing and process control instrument 300, as described below.

Figure 2:
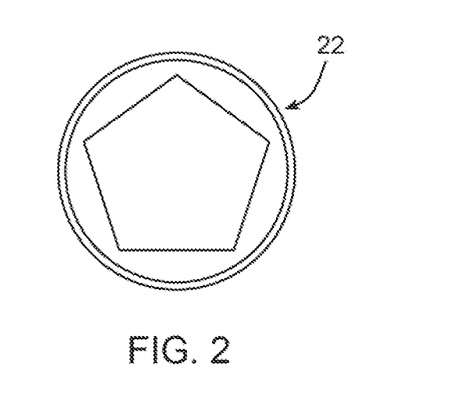
FIGS. 2 and 3 are plan views of orifice plate.
Figure 3:
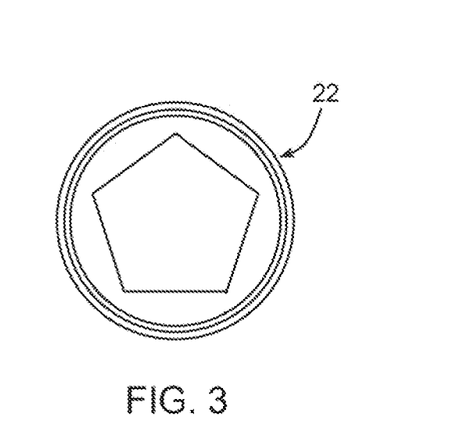
Figure 4:
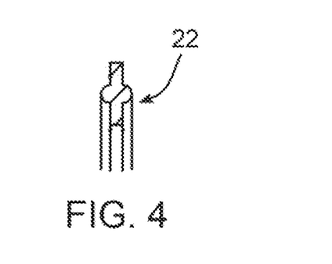
FIG. 4 is a sideview of the orifice plate of FIG. 3.

As shown in FIGS. 2 and 3, the orifice plate 22 has a generally circular outline that conforms dimensionally to the flanges of the connection interface 20 and is provided with a pentagonal orifice. As shown in FIG. 4, the rim of the orifice plate 22 is thinned on both sides for optimum mating with the connection interface 20. In general, the orifice plate 22 is fabricated from a PTFE ("Teflon") material or equivalent with the orifice functioning to constrain the flow of any gases/vapors from the headspace so as to maintain a pressure range that is appropriately matched to a pressure sensor P in the pressure sensing and process control instrument 300, as explained in more detail below. As shown in the following table and for the standard connection interface sizes (i.e., 2-, 3-, and 4-inch fittings) the orifice plate 22 can include a 60% opening and a 75% opening; in the table below, the length of one of the five linear sides of the pentagonal orifice is presented for the three common fitting diameters and for the 60% and the 75% opening choices. Other opening configurations are possible depending on the fermentation tank size and the fermentation rate.

| Connector Interface | 60% open | 75% open |
| --- | --- | --- |
| 2-inch | 0.981" | 1.097" |
| 3-inch | 1.505" | 1.682" |
| 4-inch | 2.028" | 2.267" |

While the preferred embodiment of the orifice plate 22 uses a pentagonal orifice to prevent or minimize audible "whistling," other orifice shapes are suitable, including a circular orifice.

A preferred embodiment of a pressure sensing and process control instrument 300 includes a pressure sensor P designed to sense pressures in the range typically experienced during the fermentation process; a suitable pressure sensor P is available from Setra Systems, Inc. of Boxborough Mass. 01719 under the Model 2651025WD2BT1C differential pressure transducer and having a 0-25" $H_2O$ operating range. The output of the pressure sensor P is provided as an analog value to a processing circuit that includes an analog/digital converter ND, a microprocessor μP, a display D, a power conditioner PC, a USB interface, a wireless communication link, such as a 802.11a, b, and/or g Wi-Fi link (as well a successor standards), and a network interface (i.e., RJ-45 connector). Additionally, the pressure sensing and process control instrument 300 includes a power supply PS that supplies DC power to a rechargeable battery (i.e., Li-ion), which, in turn, provides power to the power conditioner PC that conditions the battery power for the pressure sensor P and the microprocessor μP as well as the analog/digital converter ND, the USB port, the Wi-Fi link, and the network interface. The microprocessor pP includes parallel and/or serial digital inputs, an on-chip central processing unit, a clock CLK, various registers, and on-chip memory for storing firmware and/or software and data. Suitable processors include general purpose programmable processors having various bit-width buses (8-bit, 16-bit, etc.) as well special purpose processors including RISC processors and programmable logic arrays. While not shown, additional memory 302 may be provided within the processing circuit for the storage of data including long-term data history. The microprocessor μP executes its firmware or software cycle, as explained below.

As shown on the left in FIG. 1, the VOC recovery system 200 includes, as principal components, a condensation device(s) CD, a recovered condensate container or reservoir CR, a chilled fluid or refrigerant fluid source CFS, and a circulation pump CP for causing the circulation of the chilled fluid or refrigerant through the condensation device(s) CD.

The condensation device(s) CD typically includes internal passages through which a chilled-fluid (liquid or gaseous) is passed to remove heat from the surfaces in thermal communication with those surfaces chilled by the fluid. As explained in more detail below, a propylene glycol mixture, chilled brine (or an equivalent fluid) at a temperature in the 10° F.-40° F. range can be passed through the condensation device CD to effect the desired condensation.

A tap-off pipe or conduit or bleed-off line 12 extends from a tap-off hole or port (not shown) in the top portion of the fermentation vessel FV to an inlet or inlets of the condensation device CD. As explained below, the bleed-off line 12 accommodates the transfer of gases and/or vapors in the headspace HS as a general function of $CO_2$ production within the fermenter vessel FV.

The connection of the bleed-off line 12 to the fermenter vessel FV can include a cover attached to the fermenter access hatch, a flanged coupling, or other methods to provide a relatively air-tight connection to maintain headspace HS pressure. The bleed-off line 12 is a preferably conventional, EtOH-resistant, food-grade hose with a diameter typically in the 1-5 inch range, scaled to the size of the fermentation vessel; for larger fermenter tanks with a capacity of 600,000-1,000,000 gallons, approximate cross-sectional hose diameters in the six- to eight inch range are suitable. The line 12 can have a circular or non-circular interior-flow cross-section, the interior walls defining the inside lumen can have varying or non-varying surface roughness characteristics, the inside cross-section can vary significantly with length as a consequence of step-increases or decreases in diameter and varying diameters consequent to the use of varying type of straight and non-straight couplings or fittings, etc. Additionally, the conduit or pipe can be fabricated from a rigid piping, semi-rigid piping having a measure of flexure, and/or flexible piping fabricated from a plastic or elastomeric material. The flow rate through the bleed-off line 12 with time varies as a function of the $CO_2$ production to maintain a desired equilibrium within the headspace HS during those critical periods of the fermentation process so that some of the VOCs, particularly ethanol, can be removed from the process and captured without impacting the quality of the product being produced.

In the fermentation process, the yeast component metabolizes sugars in the starting material with the process proceeding on a day-by-day basis until completion. The fermentation process generates $CO_2$ and EtOH in direct proportion to one another in the liquid must with the gases/vapors in the headspace HS at a temperature of 60-90° F. or so during the process. The production of ethanol and $CO_2$ is directly proportional during fermentation due to yeast metabolism in the must. The release of $CO_2$ and ethanol into the headspace HS is governed by the solubility of the $CO_2$ and EtOH in the must, as well as the relative vapor pressure under non-ideal gas conditions. The rise of $CO_2$ precedes that of EtOH in the headspace HS and functions to carry the EtOH as a co-evolved exhaust vapor through the bleed-off line 12. The volume of emitted $CO_2$ provides an effective source of driving energy since the potential volume of $CO_2$ gas during the course of a full fermentation is approximately 55-58 times ($L_{gas}/L_{fluid}$) that of the starting volume of the must, without secondary volumetric adjustment for water vapor. In general, a bleed-off line 12 having a flow cross-section sufficient to move gaseous/vaporous components at a pressure of about 0.50 psi is adequate.

Figure 1A:
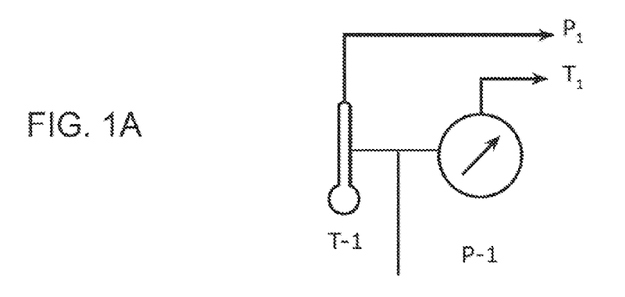
FIG. 1A is a detail of a temperature sensor and a pressure sensor

The bleed-off line 12 is instrumented with a temperature sensor T-1 (such as thermistor or thermocouple) to monitor the temperature of the vaporous/gaseous flow from the headspace HS. In a similar manner, a pressure indicator P-1 is used to monitor headspace HS and line pressure and may be used to maintain a pressure lower than the design static pressure limits of the fermenter vessel FV. AS shown in FIG. 1A, the temperature sensor T-1 and the pressure indicator P-1 can provide electrical outputs $T_1$ and $P_1$ indicative of the sensed temperature and pressure for use in data-logging, data display, and for control functions. One or both outputs can be in analog or digital form and, if desired, any analog outputs can be converted to digital form by appropriate analog-to-digital converting and conditioning circuitry.

A pressure-vacuum relief valve PVR is connected to the bleed-off line 12 and functions as a primary safety device for the fermenter vessel FV. A flow indicator or meter FM connected to the bleed-off line 12 can take the form of a vertically aligned transparent tube with a tapered thru-passage with a "float" that rises with increased flow, or a digital or analog flow meter. An emergency bypass valve EBV, such as a power-actuated damper with fail-safe spring return to open, is designed to vent the flow from the fermenter FV and the bleed-off line 12 should excessive pressure build in the fermenter vessel FV or bleed-off line 12 or in the event of a fermentation tank foam-over or should other safety sensors trigger and therefore cause the damper to open to fail-safe.

Figure 1B:
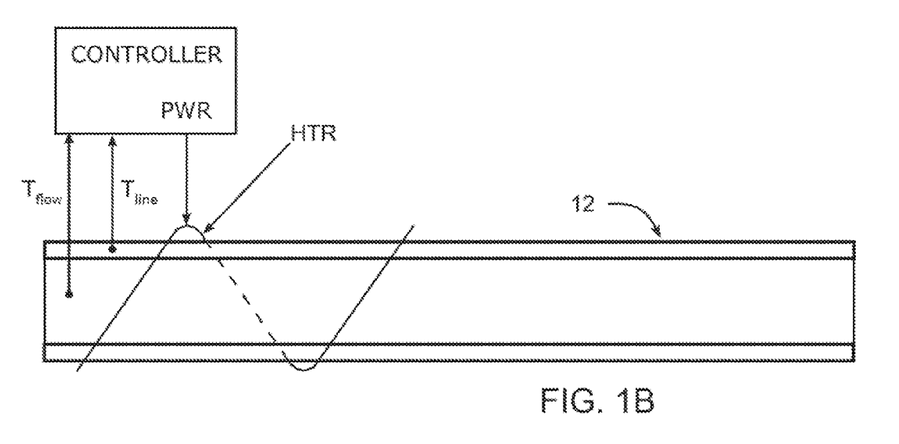
FIG. 1B is a detail of a heat conduit and its temperature controller.

A heater HTR may be provided for the bleed-off line 12 to minimize or prevent condensation in the bleed-off line 12 and is shown in FIG. 1 as a sinuous line enwrapping the bleed-off line 12. Condensation above some minimal amount in the bleed-off line has the potential of changing the equilibrium in the headspace HS that could affect product quality and has the potential to allow liquid EtOH to back flow into the must; additionally, the refluxed condensate returned to the fermenter vessel FV will contain acetaldehyde (and other compounds) that could adversely impact the quality of final alcoholic beverage (typically, wine). The heater HTR may take the form of a resistive wire or tape that is wrapped about the bleed-off line 12. The heater HTR can be 'open-loop' in which the electrical flow through the resistive heating element is set to some temperature to maintain the bleed-off line 12 at some temperature above the temperature of the flow therethrough sufficient to minimize condensation in the bleed-off line 12. In general, maintaining the temperature of the bleed-off line 12 four to six ° F. greater than the temperature of the flow therein should be adequate to minimize condensation in the bleed-off line 12 for most applications, although a larger differential may be indicated in some instances. As shown in the detail of FIG. 1B, active temperature control is also contemplated by which the temperature of the line and the flow therein are sensed and appropriate signals (analog or digital) are provided to a controller, which, in turn, provides appropriate power to the heater HTR to maintain the desired temperature differential. As shown on the right in FIG. 1B in a representative fashion, all or some portion or portions of the bleed-off line 12 can be insulated to conserve heat, especially in those situations where the fermenter vessel FV is located in an exterior location. Additionally, the bleed-off line 12 can be positioned so as to lead away from the fermenter vessel FV in monotonically declining manner so that no condensed liquid will back into the fermenter vessel FV thereby eliminating the need for a heating function.

In FIG. 1, the heater HTR is shown as a single heater element extending substantially along the entire length of the bleed-off line 12 from the fermenter vessel FV to the first of two branch points prior to the condensing device CD. If desired and depending upon the application, the bleed-off line 12 can be divided into sections and an individual heater HTR can be used for each of the plural sections. In FIG. 1B, the controller may take the form of a 'local' controller or be part of a system-wide controller as explained below in relationship to FIG. 5.

The preferred heater arrangement for the bleed-off line 12 has been described as an electrically powered heater externally wrapped or entwined with the bleed-off line 12. Other arrangements are equally suitable, including the use one or more electrically-powered cartridge heaters in the interior lumen of the bleed-off line 12 to prevent condensation therein. As an alternative, the bleed-off line 12 can be placed in a heat transfer relationship with a source of heated air (from one or more thermostat-controlled forced-air heaters) or heated water to accomplish the heating function.

While heat input to the bleed-off line 12 is preferred, especially in those installations where the fermenter is not housed in a building (i.e., outdoor installations) and/or is otherwise exposed to night-time temperature drops sufficient to cause more than inconsequential condensation in the bleed-off line 12, there may be circumstances in certain installations in which there is no need for any external heat input to the bleed-off line. For example, in certain fermenter configurations, the daily temperature during the fermentation cycle may be somewhat higher than that of the gas/vapor flow in the bleed-off line thus minimizing condensation in the bleed-off line 12 or the bleed-off line may be relatively short such that the quantity of any condensate forming therein is inconsequential, and/or the routing of the bleed-off line to the condensation device is such that most, if not all, condensates formed therein will flow away from the fermenter toward the condensation device.

Figure 1C:
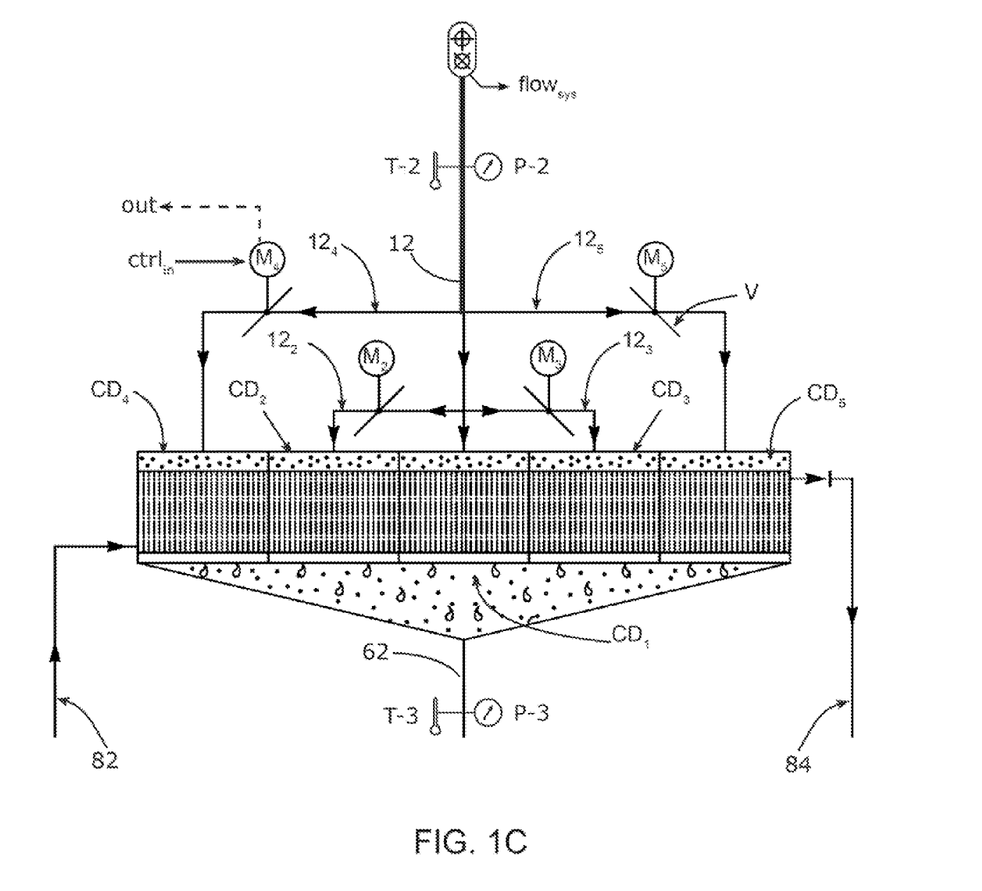
FIG. 1C is an enlarged detail of a condensing device shown in FIG. 1.

The condensing device CD is shown in a preferred form in FIG. 1C as having five condenser modules $CD_1$, $CD_2$, $CD_3$, $CD_4$, and $CD_5$. As can be appreciated, additional condenser modules (or fewer condenser modules) can be used depending upon the particular application. In the embodiment of FIG. 1 and as shown in FIG. 1C, the bleed-off line 12 branches into lines $12_4$ and $12_5$ which enter the respective headspaces of the condenser modules $CD_4$, and $CD_5$. In a similar manner, the bleed-off line 12 further branches into lines $12_2$ and $12_3$ which enter the respective headspaces of the condenser modules $CD_2$, and $CD_3$. Thus, that portion of the bleed-off line 12 that connects to the condenser module $CD_1$ and the branch lines $60_2$, $60_3$, $60_4$, and $60_5$ functions as a type of distribution system or manifold.

Each of the branch lines $60_2$, $60_3$, $60_4$, and $60_5$ includes respective selectively controllable power-actuated dampers $M_2$, $M_3$, $M_4$, and $M_5$. As represented by the exemplary damper $M_4$ in FIG. 10, each damper $M_n$ includes an input "$ctrl_{in}$" by which command signals selectively control the damper actuator or motor and, as shown in dotted-line, can include an output signal that outputs the open/close or other operational state of the damper. The various dampers are actuated as needed in response to exhaust flow variation and are used to divert gas flow from the primary bleed-off line 12 to one or more of the available condenser modules $CD_2$, $CD_3$, $CD_4$, and $CD_5$ in order to optimize EtOH collection under the time-varying flow conditions characteristic of natural fermentation. The dampers can be of the type having a movable panel or vane V that is movable between open/close positions in response to their control actuator or motor or can be of the type in which the flow control vane can be moved to one or many available intermediate positions to provide proportionate flow diversion. Regardless of the type of flow control or diverter device used, the controllable dampers M allow for the controlled distribution of the vapor/gas from the fermenter vessel FV to one or more of the condenser modules $CD_2$, $CD_3$, $CD_4$, and $CD_5$ to provide a dynamic re-distribution or re-balancing of the vapor/gas flow from the fermenter vessel FV into the condenser modules throughout the fermentation process. Thus, the condensing capacity of the condensing device CD is variable and can be increased in stages by making one or more of the condenser modules $CD_2$, $CD_3$, $CD_4$, and $CD_5$ available to the flow from the bleed-off line 12 to effect condensing thereof and decreased in stages by closing off one or more of the condenser modules $CD_2$, $CD_3$, $CD_4$, and $CD_5$ from the flow from the bleed-off line 12.

The power-actuated dampers $M_2$, $M_3$, $M_4$, and $M_5$ can be controlled by a central controller, described below, in response to 'flow' signal(s) provided by the flow meter FM and, if desired, by the differential pressure across the condensation device CD as provided by pressure sensors P-2 and P-3 (FIG. 1C), and/or a predetermined control profile that reasonably reflects the gas/vapor flow from the headspace HS of the fermenter vessel FV.

The temperature sensor T-2 (FIGS. 1 and 1C) may be used to verify the incoming gas temperature and as a differential temperature indicator across the condenser CD. The pressure sensor P-2 may be used to verify proof-of-flow, monitor inlet pressure to the condenser CD, and, along with the pressure sensor P-3, monitor differential pressure across the condenser CD.

The gases and/or vapors from the headspace HS are conducted via the bleed-off line 12 into the condenser device CD where the ethanol and other VOCs, and all or some of the water content, are condensed out of the gas/vapor stream to yield an ethanol-rich mix of liquid droplets that accumulate in the lower end of the condenser device CD and are passed via line 62 into the ethanol collection tank CR. Once the ethanol, other VOCs, and all or some of the moisture content are "wrung" from the gas/vapor stream, that stream is substantially reduced to $CO_2$ gas. As shown in FIG. 1, the carbon-dioxide exits the ethanol collection tank CR via a vent pipe or conduit 64 for venting to the atmosphere or, alternatively, for recovery for other industrial uses or uses in wine-making processes.

The ethanol collection tank CR is instrumented with a liquid level sensor 70, which can be either of the electronic or mechanical type and which outputs a signal "level" as shown. Additionally, a temperature sensor T-4 outputs the temperature in the space above the level of the liquid, and a temperature sensor T-5 outputs the temperature of the liquid condensate. A pressure sensor P-4 provides pressure information within the ethanol collection tank CR; in general, it is expected that the pressure sensed will be near atmospheric pressure. Lastly, the liquid condensate can be drained from the ethanol collection tank CR via a drain valve 66. In general, the system of FIGS. 1-1C will remove a minimum of about 35% and a maximum of over 95% of the ethanol from the flow from the headspace HS and the aggregate flow restriction of the flow path and the condensing device is insufficient to cause normal operating pressures no more than about 0.50 psi (about 14" $H_2O$) rise in the pressure within the fermentation vessel FV.

If desired, a second chilled-surface condenser can be connected to the $CO_2$ output line 64 (FIG. 1) to receive the $CO_2$ output from the headspace of the condensate collection tank CR to 'wring' any residual VOCs therefrom prior to the release or capture of the $CO_2$ to thereby increase system efficiency.

In FIG. 1, the ethanol collection tank CR is shown in a symbolic fashion; in practice, the ethanol collection tank CR may take the form a sealable canister(s), tank(s), or drum(s) that conforms to industry, state, and/or federal requirements for the secure collection and transport of ethanol by appropriately licensed personnel or agent.

The cooling fluid source CFS contains a chilled fluid (such as brine, glycol, air, nitrogen, etc.) that connects via an external pump CP for causing the circulation of the chilled fluid through a pipe 82 to the condensation device(s) CD and a branch pipe 82*a* to chiller coils (not shown) in the condensate recovery tank CR to maintain satisfactory conditions within the condensate recovery tank CR. The chilled fluid is returned from the condensation device CD via a pipe 84 and from the condensate recovery tank CR via a branch pipe 84*a* to the chilled fluid source CFS. The chiller/external pump arraignment shown is preferred; however, other arrangements are suitable as disclosed in the above incorporated U.S. patent application Ser. No. 12/476,231 filed Jun. 1, 2009.

As shown in FIG. 1, the cooling fluid feed line 82 can be instrumented with temperature/pressure sensors T-6/P-6 and the fluid feed line from the chiller CFS to the circulation pump CP can likewise be instrumented with temperature/pressure sensors T-7/P-7. In a similar manner, the cooling fluid return line 84 can be instrumented with temperature/pressure sensors T-8/P-8 and the fluid return line 84*a* from the condensate tank CR chiller CFS to return line 84 can be instrumented with temperature/pressure sensors T-9/P-9.

The system 100 of FIG. 1 can be operated in a manual mode in which the operational temperature of the heater HTR (when used) is set and in which the flow or mass flow information from the flow meter FM is monitored with the various dampers $M_2$, $M_3$, $M_4$, and $M_5$ operated to distribute flow to additional condenser modules $CD_2$, $CD_3$, $CD_4$, and $CD_5$ as needed.

Figure 5:
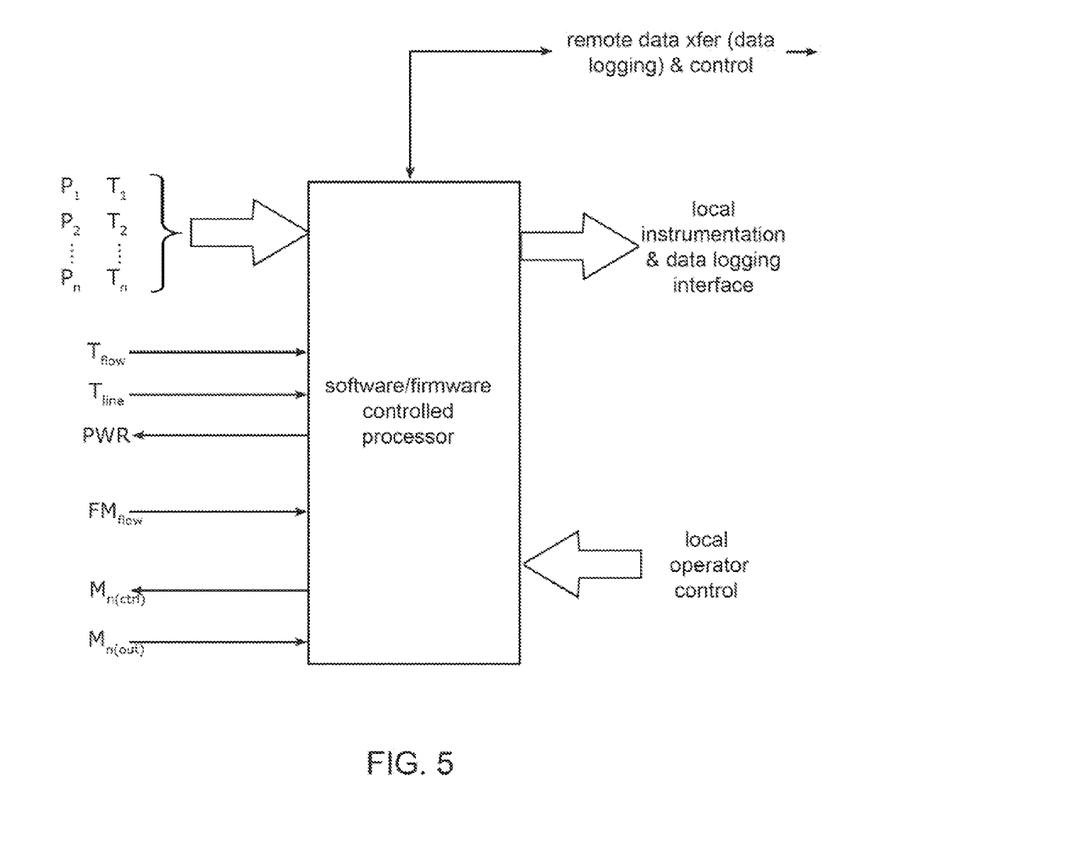
FIG. 5 is an example processor-based arrangement for the semi-automation or automation of a portion of the control function(s) of the system of FIG. 1.

The system 100 is also amenable to semi- or full-automated control using a stored-program processor or microprocessor. For example and as shown in FIG. 5, a software or firmware controller processor or microprocessor (μp) accepts all (or some sub-set) of the $P_1$, $P_2$, . . . . $P_n$, and $T_1$, $T_2$, . . . . $T_n$ data, the flow information signal 'flow' from the flow meter FM as well as other inputs including the 'level' signal from the level sensor 70 and the damper position signals 'out' (indicative of the open, closed, or some intermediate operating state of the various dampers) and provides appropriate control signals to the various dampers $M_2$, $M_3$, $M_4$, and $M_5$ to distribute flow to additional condenser modules $CD_2$, $CD_3$, $CD_4$, and $CD_5$ as needed. Additionally, the processor can effect data-logging and provide an instrument readout interface for a system operator. Further, operator controls can be provided to control or override certain aspects of the system operation. For those applications in which multiple fermenters are in operation, some of which may be at different stages in the fermentation process, a telecommunications link can be provided for communicating information to a central location and, if desired, for receiving operational commands therefrom. The telecommunications link can take the form of conventional wired (copper or optical) or wireless links (WiFi) using conventional network protocols (Ethernet, IP, etc.). The software may be hosted on an operating system communicating with other software and/or hardware components in the system.

FIG. 5 shows inputs for the $T_{flow}$ and $T_{line}$ values associated with the bleed-off line 12 heater HTR and a corresponding PWR input for the heater. As mentioned above in relationship to FIG. 1*b*, the heating of the bleed-off line 12 can be addressed locally or can be addressed in the processor of FIG. 5.

The processor can take the form of one or more firmware- or software-controlled microprocessors or microcomputers (as well as special-purpose processors, including RISC processors), application specific integrated circuits (ASIC), programmable logic arrays (PLA), discrete logic or analog circuits, and/or combinations thereof.

The software or firmware driving the processor can provide output signals to the various dampers M as the quantitative value of the 'flow' signal from the flow meter passes above or increments above various set-points to thereby provide the control signals to the various dampers $M_2$, $M_3$, $M_4$, and $M_5$ to distribute flow to additional condenser modules $CD_2$, $CD_3$, $CD_4$, and $CD_5$ as needed. Conversely, as the quantitative value of the 'flow' signal from the flow meter passes below or decrements below various set-points, the processor can thereby provide the control signals to the various dampers $M_2$, $M_3$, $M_4$, and $M_5$ to proportionately reduce or to cease distributing flow to the various additional condenser modules $CD_2$, $CD_3$, $CD_4$, and $CD_5$.

Figure 6A:
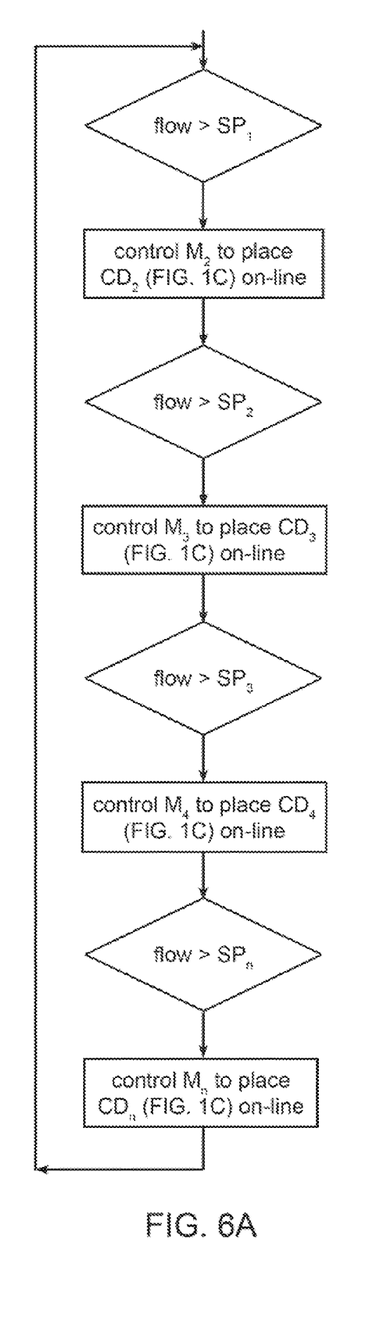
FIGS. 6A and 6B are example flow diagrams showing the manner by which condensation capacity is made available or removed during the fermentation process.
Figure 6B:
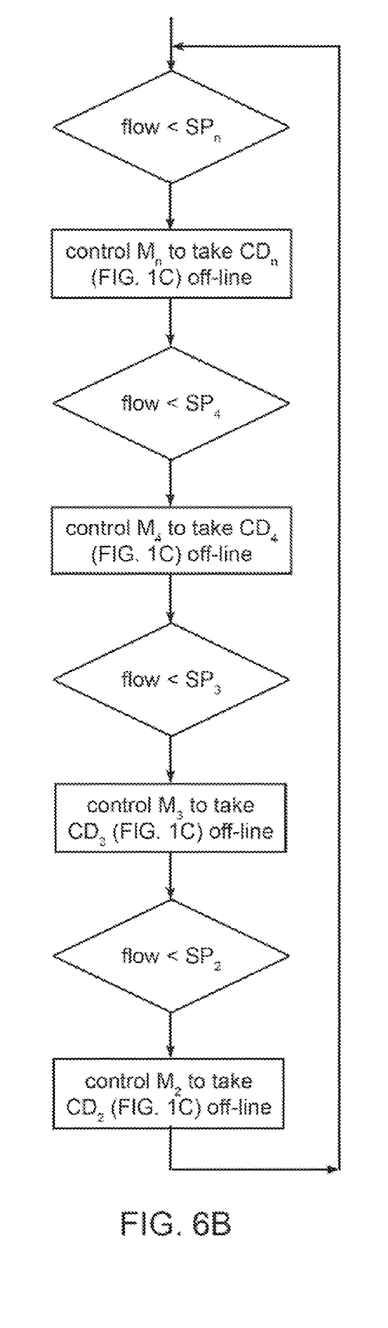

FIGS. 6A and 6B represent exemplary control sequences; in FIG. 6A, set points $SP_1$, $SP_2$, . . . $SP_n$ are established with a query presented as to whether the set point has been exceeded or not. As the processor cycles through its flow sequence and in those cases where a set point SP has been exceeded, a control signal is sent to the appropriate damper M to open the damper to place a corresponding condenser module on-line. In FIG. 6B, the processor cycles through the flow sequence and in those cases where the flow value is no longer above the set point SP, a control signal is sent to the appropriate damper M to close the damper M to take a corresponding condenser module off-line.

While the various dampers M can be operated in an on/off manner to provide an increase or decrease in condensation capacity in a 'step-wise' manner, the various dampers can also be operated in a proportional manner to provide a proportional increase or decrease in condensation capacity.

If desired, a measure of hysteresis can be programmed into the control sequence. Thus, a command to any one or more of the dampers M can be delayed until the measured value exceeds a particular set point (FIG. 6A) or decreases below a particular set point (FIG. 6B) for a selected period of time ranging from seconds to minutes.

The set points $SP_n$ can be established as a function of flow (e.g., flow>$SP_n$ or flow<$SP_n$ as shown in FIGS. 6A and 6B), sensed pressure (e.g., P>$SP_n$ or P<$SP_n$), and/or some direct or indirect combination thereof (i.e., f(flow,P)>$SP_n$ or f(flow,P)<$SP_n$) or some other parametric proxy that is functionally related to the gas/vapor flow from the headspace HS during the fermentation process. Additionally, the processor can function in full or partial response to some predetermined control profile that reasonably reflects the gas/vapor flow from the headspace HS of the fermenter vessel FV throughout the fermentation cycle.

In the embodiment described above, a single fermenter vessel FV supplies gas/vapor from its headspace HS during the fermentation cycle to the condensation device CD. In practice, wineries often have multiple fermenter vessels in simultaneous or near simultaneous operation.

While the system described changes condensation capacity as a function of some parametric value, in some applications where experience shows a certain level of fermentation process predictability with time, it may be desirable to pre-program the changes in condensation capacity with time from the start of the fermentation process and/or pre-program the changes in condensation capacity to correspond with the various stages of the fermentation process and do so with or without consideration of the flow volumes, pressures, etc.

As can be appreciated, the system is sized to stay within a safety factor for allowable fermenter pressure in a closed winery fermenter, where common art has relief valves PVR typically set at about 0.85 psi (or 24" WC). The system 20 as designed is sized to allow for a calculated maximum instantaneous flow rate for a given fermenter tank size, as current art, and to allow pressure build-up of no more than about 0.50 psi (or 14" WC). Major contributors to static pressure in the system are primarily the condenser CD, the size and length of the bleed-off line 12, and smoothness of internal surfaces throughout the system. Other factors include inlet and outlet losses, static effects of fittings, temperature, and the gas/vapor density. As can be appreciated, the system is usable in situations in which the pressure build-up is greater than the above described 0.50 psi (or 14" WC).

The system 200 operates at low-pressure for an emission control system, using the emitted $CO_2$ to provide the driving energy to push flow through the collection system. An advantage of the low pressures characteristic of this system is that premature in-line condensation is minimized, thereby greatly reducing the possibility that condensate will flow back (i.e., reflux) into the fermenter vessel FV and affect the quality of the product, since the refluxed condensate will include acetaldehyde (and other compounds) that could adversely impact the quality of final alcoholic beverage. In the described system, the condenser CD produces the greatest static pressure drop in the system and is therefore the controlling element; while the conduit sizing and length are of secondary importance in their contribution to static pressure. For the design of any specific application, turbulence and Reynolds Number is calculated throughout the system, but serves primarily as a secondary check for the maximum instantaneous design flow condition.

Gas/vapor-flow volumes through the system change temporally, starting with zero flow at the start of fermentation and rising to a maximum flow rate. As sugars are consumed in the must, the gas/vapor-flow volumes diminish until fermentation is complete. The system is sized to accept the maximum instantaneous flow rate, in addition to the variable flow and exhaust gas composition encountered during the fermentation cycle.

Initially and when the must is first inoculated with yeast, the fermentation activity is minimal and most of the evolved $CO_2$ and EtOH are dissolved in the must. Flow out of the condenser CD only begins after fermentation has proceeded for a period of time and therefore a decision must be made about when to start EtOH collection. A reasonable practice is to initiate use of the device within 24 hours following yeast inoculation, or by the time there is a 1° Brix reduction, a 2° F. rise in must temperature, or an EtOH concentration in the must that exceeds 3%, whichever occurs first and as in this art, depends on the measurements normally taken by the wine-maker. This practice will ensure that the operation of the system does not interfere with the initial aerobic phase of fermentation and that collection is initiated before a significant amount of EtOH has escaped collection. An additional advantage of the low pressures in this system is reduced premature in-line condensation that might cause condensate to flow back to the fermenter vessel FV.

Average conduit velocities are designed in the system to be approximately 1000-3000 fpm. Because of static pressure limitations, as described above, the system and conduit velocities should not exceed 4000 fpm and ideally should operate nearer an average of 1500 fpm. Velocities in excess of 4000 fpm typically result in excessive static pressure that may cause premature in-line condensation or an excessive buildup of static pressure. Initial flows may be below 1000 fpm; however, flows will quickly rise above 1000 fpm as $CO_2$ emissions begin to increase during fermentation. Once fermentation flows in excess of 1000 fpm are attained, the target range of around 1500 fpm is maintained by selected operation of the various dampers $M_2$, $M_3$, $M_4$, and $M_5$ to distribute flow to additional condenser modules $CD_2$, $CD_3$, $CD_4$, and $CD_5$ as needed to maintain static pressures, as described herein in relationship to FIGS. 4, 7, and 8 or selected increases or decreases in condensation capacity.

The system 200 is designed to reduce the potential for premature condensation of EtOH in the bleed-off line 12 by use of the heating feature, described above. The gas-vapor mixture exiting the fermenter vessel FV is maintained at a temperature somewhat above that of the headspace HS by the heated bleed-off line 12, sufficient to prevent or reduce in-line condensation. The temperature of the bleed-off line 12 is preferably regulated at or slightly above headspace HS temperature to thereby minimize the cooling demand on the condenser CD and therefore minimize energy use.

That portion of the bleed-off line 12 that extends into the condenser CD functions as a distribution manifold that transfers gases evolved from the fermenter vessel FV to the condenser CD modules via the various branch lines. As the gas pressure increases in the manifold portion, the pressure sensing device P-2 provides an output sufficient to command or trigger a power-actuated shut-off damper $M_n$ to open at a predetermined pressure. This newly opened branch of the manifold portion will reduce the bleed-off line 12 pressure, fermenter HS headspace pressure, and the velocity through the condenser CD to maintain the desired maximum headspace HS pressure and maximum effective design velocity and pressure through the individual condenser modules $CD_1$, $CD_2$, $CD_3$, $CD_4$, and $CD_5$ as needed. The manifold portion is designed with sufficient branch conduits and condenser modules $CD_n$ to efficiently handle the maximum calculated gases evolved from the fermentation process plus some safety factor. As the pressure continues to increase, additional power-actuated damper(s) $M_n$ will open to distribute the gas/vapor thereby decrease the pressure. Conversely, as the pressure from the fermenter vessel FV decreases to a predetermined pressure, the pressure sensing device P-2 will trigger the appropriately power-actuated damper(s) $M_n$ to close, thereby increasing the pressure in the manifold portion and maintaining a desired minimum design velocity through the condenser modules $CD_n$.

In some applications the flow of $CO_2$ and EtOH over the chilled-surfaces of the condensing device may result in laminar flow at the vapor/chilled-surface interface. In some applications, it may be desirable to limit the formation of laminar flow regions to improve heat transfer therebetween and thus improve condensation efficiencies. Laminar flow regions can of prevented from forming or dissipated after formation by providing the chilled-surfaces with sufficient surface roughness, spine-like projections, projecting edges, grooves, channels, etc. to prevent, minimize, or dissipate laminar flow at the vapor/chilled surface interface. If desired, turbulence can be introduced by a separate fan-like device or an air-flow "stirring" device.

If desired, further steps can be taken within the plenums described above to enhance the transfer of the EtOH into a liquid form. For example, a high-pressure, low-volume water injector(s) can spray a very fine water fog into the plenum to (a) pre-cool the $CO_2$ and EtOH flow and (b) adsorb ethanol vapor. In some applications, it may be desirable to introduce a minimal amount of water or other liquid to slightly dilute the collected ethanol to thereby enhance the capture efficiency. The addition of a fluid spray would be suitable where emission control and offset credits are paramount.

In the process of natural fermentation, $CO_2$ and EtOH are co-evolved into the must in equal molar amounts as described above. However, the release into the fermenter headspace HS and to the atmosphere is governed by physical and chemical properties of the two compounds in the liquid must, the air/gas interface, and the open atmosphere. It is the substantial volume of $CO_2$ released that provides the driving energy to passively "push" the EtOH—$CO_2$ gas/vapor mixture through the conduits and condenser.

Release of EtOH to the atmosphere is more complicated than that of $CO_2$ due to the relatively high solubility of the alcohol in the liquid must. Emission of EtOH is governed, among other factors, primarily by the temperature of the fermentation, with hotter fermentations causing greater release of EtOH into the headspace. White wine is generally fermented at lower temperatures than red wine, both having similar sugar consumption. Another significant factor affecting emission of EtOH is the presence of a solid grape skin cap (known in the industry as pomace) that floats to the top of the must, as is typical in fermentations of red wine. The cap is also responsible for causing temperature inhomogeneities within the fermenter due, in part, to a higher concentration of yeast.

The VOC recovery arrangement 200 shown in FIG. 1 uses the evolved gasious $CO_2$ as the driving energy to transport the EtOH and water vapor through the system; however, there are circumstances, such as a slow or sluggish fermentation process or an over-active fermentation process that can compromise the quality of the wine or other alcoholic beverage and necessitate the need for positive control of the fermentation process.

Figure 7:
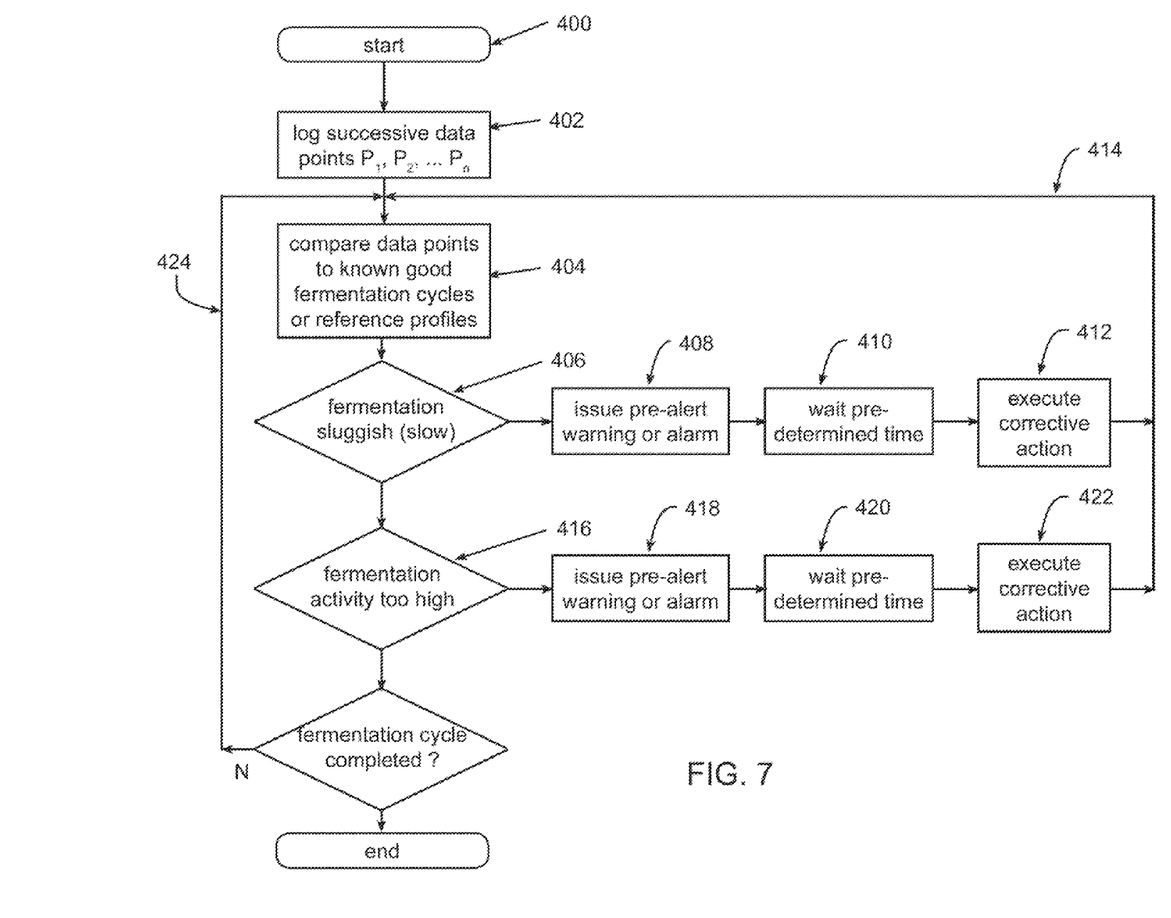
FIG. 7 is an example process flow diagram illustrating operation of the pressure sensing and process control instrument.

As shown on the right in FIG. 1, the above-described pressure sensing and process control instrument 300 is in fluid communication with the pressure within the headspace of the fermentation vessel FV through conduit 28 via port P with the above-described microprocessor μP executing a firmware or software cycle as shown in a generalized fashion in FIG. 7.

As shown, the sequence is started at 400 followed by the logging of successive data points at pre-selected time intervals. The sensing and logging data $P_1, P_2, \ldots P_n$ can take place, for example, every 10 minutes. In addition to storing each successive data point, the successive data points can be displayed as a graph over time on the display D. When a sufficient number of data points are logged, the data points can be compared to data points from a reference or exemplar fermentation cycle or from one or more known good data points from prior fermentation cycles. As can be appreciated, reference fermentation cycles or data from known good prior fermentation cycles for various types of starting materials, fermentation vessel capacities, etc. can be stored in a library kept in memory. As shown at step 406, if the data point comparisons show a trend toward slow (i.e., "sluggish") fermentation, a pre-alert warning or an alarm can be issued (based upon the variance between the measured data points and the exemplars) and, if the wine maker does not intervene to correct the situation after a suitable waiting period (step 410), some type of corrective action and be taken at step 412. In the case of a slow fermentation that results from an inhomogeneity of the contents of the fermentation vessel, rotatable paddle-type mixers MX (FIG. 1) can be operated to mix the contents of the fermentation vessel or pumps (not shown) activated to pump material from the bottom of the fermentation vessel FV and discharge or spray the so-pumped material into the headspace HS thereof with the processing sequence returning via pathway 414 to step 404 to repeat the measuring and comparing cycle. Conversely, if the data point comparisons show a trend toward a high-activity fermentation, a pre-alert warning or an alarm can be issued at step 418 (based upon the variance between the measured data points and the exemplars) and, if the wine maker does not intervene to correct the situation after a suitable waiting period (step 420), some type of corrective action can be taken can be taken at step 422. In the case of a high-activity fermentation, multi-loop cooling coils surrounding the fermentation vessel FV or heat exchange cooling coils (not shown) within the interior fermentation vessel FV can be activated to lower the temperature of the mix and thereby lower the fermentation activity with the processing sequence returning via pathway 414 to step 404 to repeat the measuring and comparing cycle. In the event the fermentation process is within expected bounds, the process simply loops via pathway 424 until the fermentation cycle is completed. The cooling coils can accept chilled fluid from the chiller CFS that is part of the VOC recovery system 200 or from a separate chilled fluid source (not shown).

While the preferred embodiment has been shown as a single fermentation vessel FV, as can appreciated, multi-fermentation vessel systems are possible and as shown in FIG. 6, the pressure sense line 28 from n fermentation vessels $FV_1, FV_2, \ldots FV_n$ connect to a 1-of-n manifold 300 by which a selection signal from the pressure sensing and process control instrument 100 sequentially selects each fermentation vessel $FV_1, FV_2, \ldots FV_n$ for data logging.

Since the pressure sensing and process control instrument 100 includes a USB port, all data collected by the pressure sensing and process control instrument 100 can be downloaded for storage or transfer to another device. Additionally, data can be transmitted over the Wi-Fi link to a hub for uploading to a central computer or transferred by the network ethernet port (RJ-45) that can include Internet functionality. As can be appreciated, the Wi-Fi link and the network link also facilitate transmission of pre-alert warnings or alarms to a pager, cellphone, or smartphone as needed.

As will be apparent to those skilled in the art, various changes and modifications may be made to the illustrated embodiment of the present invention without departing from the spirit and scope of the invention as determined in the appended claims and their legal equivalent.

The invention claimed is:
1. A fermentation-related control system comprising:
a bleed-off line configured to carry a head space vapor from a fermentation vessel to at least first and second condensing flow paths;
an output line configured to receive condensed fluid from at least one of the first or second condensing flow paths and a storage tank;
a distribution mechanism configured to distribute at least some of the head space vapor between or among the at least first and second condensing flow paths; and a processor configured to control the distribution mechanism as a function of flow in the bleed-off line and pressures in the bleed-off and output lines.

2. The system of claim 1, further comprising first and second pressure sensors that convey information to the processor, responsive to the pressures in the bleed-off and output lines.

3. The system of claim 2, wherein at least one of the first or second pressure sensors are configured to produce electrical pressure signals periodically.

4. The system of claim 2, wherein at least one of the first or second pressure sensors are configured to produce electrical pressure signals continuously.

5. The system of claim 1, wherein the processor is further configured to control the distribution mechanism based at least in part on a predetermined control profile.

6. The system of claim 5, wherein the predetermined control profile comprises a set point based on at least one of a flow signal or a pressure signal.

7. The system of claim 1, wherein the processor is configured to control a heater as a function of a temperature in the bleed-off line.

8. The system of claim 1 wherein the processor is configured to wirelessly communicate with at least one of a pressure sensor or the distribution mechanism.

9. The system of claim 1, wherein a processor is configured to control the distribution mechanism in a step-wise manner.

10. The system of claim 1, wherein a processor is configured to control the distribution mechanism in a continuous manner.

11. The system of claim 1, wherein the distribution mechanism comprises at least two dampers.

12. The system of claim 1, further comprising an instrument readout interface configured to display at least one of pressure, flow, or temperature information provided by the processor.

* * * * *